(12) United States Patent
Blendl (10) Patent No.: US 9,784,695 B2
(45) Date of Patent: Oct. 10, 2017

(54) TEST BODY AND METHOD FOR CHECKING THE TRANSMISSION PROPERTIES OF VOLUME TOMOGRAPHS

(71) Applicant: FACHHOCHSCHULE KÖLN, Köln (DE)

(72) Inventor: Christian Blendl, Bergheim (DE)

(73) Assignee: TECHNISCHE HOCHSCHULE KOELN, Cologne (DE)

( * ) Notice: Subject to any disclaimer, the term of this patent is extended or adjusted under 35 U.S.C. 154(b) by 454 days.

(21) Appl. No.: 14/355,135

(22) PCT Filed: Nov. 8, 2012

(86) PCT No.: PCT/EP2012/004647
§ 371 (c)(1),
(2) Date: Jul. 31, 2014

(87) PCT Pub. No.: WO2013/068118
PCT Pub. Date: May 16, 2013

(65) Prior Publication Data
US 2014/0348305 A1 Nov. 27, 2014

(30) Foreign Application Priority Data
Nov. 8, 2011 (DE) .......... 10 2011 117 859

(51) Int. Cl.
*A61B 6/00* (2006.01)
*G01N 23/04* (2006.01)

(52) U.S. Cl.
CPC .......... *G01N 23/046* (2013.01); *A61B 6/583* (2013.01)

(58) Field of Classification Search
CPC .............................. A61B 6/583; G01N 23/046
See application file for complete search history.

(56) References Cited

U.S. PATENT DOCUMENTS 6,059,700 A * 5/2000 Ellenburg .......... A63B 21/0728
482/107
6,076,966 A 6/2000 Stueve
6,364,529 B1 4/2002 Dawson
(Continued)

OTHER PUBLICATIONS

L.Franco,F.Gomez,A.Iglesias,J.Pardo,R.Lobato,J.Mosquera,M.Pombar,J.R.Sendon,F.Ledo,A.Yanez;Blurring and MTF Determination of a Radiotherapy EPID Using the Edge Spread Funtion,IEEE0-7803-8700-7/04/$20.00(C)2004 IEEE.
(Continued)

*Primary Examiner* — Dani Fox
(74) *Attorney, Agent, or Firm* — Andrew Wilford (57) ABSTRACT

The invention relates to a test body for checking the transmission properties of volume tomographs, in particular radiological tomographs, which comprises several plates (2) that are connected to form a stack, in which adjacent plates (2) contact each other and said body comprises spheres (4) made of at least one material that is different from the plates (2) and having different diameters, wherein the respective spheres (4) are arranged in and/or between at least some of the plates (2), and wherein on/in the test body, preferably in the stack, at least one rod-shaped hollow profile, in particular at least one pipe having a circular cross section, is arranged. The invention further relates to a method for checking the transmission properties of a tomograph using such a test body (1).

11 Claims, 3 Drawing Sheets

(56) References Cited

U.S. PATENT DOCUMENTS

| | | | |
|---|---|---|---|
| 6,490,336 B1 | 12/2002 | Suess | |
| 7,016,456 B2 | 3/2006 | Basu | |
| 8,666,133 B2 | 3/2014 | Vermandel | |
| 2002/0131552 A1* | 9/2002 | Nishizawa | A61B 6/583 378/65 |
| 2004/0228435 A1* | 11/2004 | Russell | A61N 5/1048 378/18 |
| 2013/0136227 A1* | 5/2013 | Ishihara | A61B 6/032 378/19 |

OTHER PUBLICATIONS

H.Kunzmann,Braunschweig,Germany,Enhancement and Proof of Accuracy of Industrial Computed Tomography (CT)Measurements,Annals of the CIRPvol. 56/1/2007.

Voigt et al, A New Phantom for Image Quality, Geometric Destortion and HU Calibration in MSCT and CBCT, Proc. of SPIE vol. 8313 83132P-1, Medical Imaging 2012:Physics of Medical Imaging.

* cited by examiner

TEST BODY AND METHOD FOR CHECKING THE TRANSMISSION PROPERTIES OF VOLUME TOMOGRAPHS

CROSS REFERENCE TO RELATED APPLICATIONS

This application is the US-national stage of PCT application PCT/EP2012/004647 filed 8 Nov. 2012 and claiming the priority of German patent application 102011117859.0 itself filed 8 Nov. 2011.

FIELD OF THE INVENTION

The invention relates to a test body, in particular a test body for checking the transmission properties of volume tomographs, in particular radiological volume tomographs that are usually, but not exclusively, used in medical diagnostics and therapy, for example radiotherapy, in oral and maxillofacial surgery, in dental implantology etc.

BACKGROUND OF THE INVENTION

The invention further relates to a method of checking the transmission properties of a volume tomograph using a test body in which a series of a plurality of measurement recordings of the test body is produced with the volume tomograph and a stack comprising a plurality of layer images of the test body is calculated from the series by a tomography algorithm or rear-projection algorithm in the volume tomograph itself or in an evaluation unit.

Within the meaning of the invention described here, tomographs, in particular volume tomographs, are understood to mean all devices with which it is possible to calculate a stack comprising a plurality of layer images of a body under examination from a series of recorded measurement values, in particular from a series of recorded images, with the assistance of the tomography algorithm or rear-projection algorithm.

At the same time, for the term volume tomograph used here, it does not matter as far as the invention is concerned which measuring principle is used as a basis for recording the individual measured values or, in the special case, for recording the images (for example in the case of an X-ray computer tomograph or a magnetic resonance tomograph).

For example, volume tomographs can replace X-rays to calculate a stack of layer images from a series of individual X-ray images, for example such images that each represent a two-dimensional projection of the X-ray absorption, after the images have been recorded, such a stack representing a three-dimensional image of the body under examination. Accordingly, in such a volume tomograph, use is made of 2D image sensors whose sensor pixels record the measured values.

Also known are magnetic resonance tomographs or magnetic resonance volume tomographs, with which so-called spin flips that lead to the transmission of electromagnetic waves that can be received by antennas and are characteristic of the material to be examined, can be produced by the action of external magnetic fields in a tissue to be examined. Here, the volume range (voxel) of the body under examination from which the received electromagnetic wave originates is determined by the superimposition of magnetic fields. These measured values can also be converted to layer images by tomography or rear-projection algorithms.

In sonography, i.e. in ultrasound examinations, it is also possible to create sonographic recordings that are based on the reflection of ultrasonic waves. Examples of further known tomographic devices are Digital Volume Tomographs (DVT) and also the following devices: Cone Beam Computer Tomographs (CBCT) or tomographs that are used to record the volume information in extremities, or devices for the spatial representation of the female breast (tomosynthesis).

For the test body, and in particular for the method according to the invention, it does not matter which kind of tomograph, preferably volume tomograph, is used, as the method relates to the evaluation of the layer images created or 3D recordings resulting therefrom.

In order to be able to draw definite conclusions relating to the particular body under examination, such as for example the different kinds of tissue or the types of material in general of the body and their dimensions, from tomographic recordings created by such above-described devices, it is necessary for the transmission properties of these volume tomographs to fulfill certain quality criteria.

As an example, the so-called Modulation Transfer Function (MTF) or contrast resolution is therefore an important quantity, based on which a conclusion can be drawn relating to the quality with which different types of tissue or materials in general of a body under examination can differ from one another, such as for example healthy tissue and tumorous tissue.

Furthermore, it is known that volume tomographs and the in particular manufacturer-specific algorithms used, like the above-described rear-projection algorithms, can lead to geometric distortions in the visual reproduction of a body under examination compared with the actual dimensions of the body. Such distortions or too inaccurate spatial resolution cannot be tolerated, especially in prosthodontics or even in radiation therapy, as here the target volume must be determined as accurately as possible in order to avoid damage to surrounding tissue. Knowledge of such distortions is also necessary, for example, when visual reproductions of the same body from different tomography systems are to be superimposed (matched).

Examples of further quality criteria are the signal-noise ratio and also the noise-power spectrum.

In the prior art, it is known to provide test bodies with which it is possible to check volume tomographs with regard to the above-mentioned criteria or transmission properties, such as for example contrast and spatial resolution. Particularly in the radiologically based planning of interventions, for example in prosthodontics or radiation therapy, the uncertainty of the position determination in the target volume must be kept as small as possible in order to protect healthy tissue.

Such test bodies are therefore used in particular to enable the contrast and spatial resolution of the volume tomographs to be tested. In so doing, it is known that such test bodies comprise structural elements that can be differentiated from the surroundings by a volume tomograph in the spatial 3D representation or the individual layer images of a layer image stack. With regard to their application in radiology, such test bodies are also referred to as radiological phantoms or as test bodies in general.

OBJECT OF THE INVENTION

The object of the present invention is to provide a method and also a test body for carrying out the method of checking the transmission properties of volume tomographs, with which it is possible using one and the same test body, in particular a test body matched to the volume tomographs to be investigated, to check the transmission properties with regard to a plurality of criteria simultaneously. For example, it should be possible to check the transmission properties with regard to contrast resolution and spatial resolution, where applicable also with regard to further criteria such as for example signal-noise ratio or noise-power spectrum.

In the following, the term tomograph will continue to be used in general, even though preferably a volume tomograph is meant.

SUMMARY OF THE INVENTION

According to the invention, this object is achieved in that the test body for checking the transmission properties of tomographs, in particular of radiological tomographs, has a plurality of plates that are connected to form a stack in which adjacent plates contact each other, and the test body has spheres made of at least one material that is different from the plates of at least two different diameters, the spheres being in or between at least some of the plates, and at least one tube is on/in the test body, preferably in the stack. Such a tube can preferably have a circular cross section perpendicular to its longitudinal extension and therefore be a round tube.

Here, in one embodiment, the plates are connected to the stack by external or internal connecting elements that can also be formed by at least one tube. The plates can be glued together for example. A possible embodiment can also provide that the plates are connected to form the stack by an above-mentioned, in particular a single, tube, for example that passes through the plates.

If the plate stack has at least one tube in its interior, preferably the at least one tube passes through at least some of the plates, where applicable also all of the plates. For example, here, the at least one tube can be have its longitudinal axis oriented perpendicular to the planes of the plates or to their contact planes. An angular deviation in the range of plus/minus 30° from the perpendicular orientation can also preferably be provided as will be explained later.

According to the invention, such a test body can be used in a method of checking the transmission properties in order to create a series of a plurality of measured value recordings of the test body by a tomograph to be tested and then to calculate a stack of a plurality of layer images of the test body from this series by a tomography algorithm in the tomograph or in a separate evaluation unit of the tomograph.

In the method according to the invention, for at least some, preferably all, layer images of the created image layer, a measure of the modulation transmission function is calculated based on the image reproduction of the cross sections of the at least one tube in the stack.

If, when checking a tomograph, the test body is positioned in such a way that, in the later visual reproduction, the at least one tube lies with its longitudinal axis perpendicular to the plane of the individual sectional views, the cross-sectional representation of this tube has a ring shape, in particular a circular ring shape, thus enabling the transmission properties of the tomograph to be tested based on this at least one tube within each sectional view of the image stack. With such a structure, this enables the test to be carried out in each sectional view based on exactly the same criteria.

Here, with such tomographs that guide a radiation source on a circular path about an axis of rotation on which the center of the circle of rotation lies, a test body is positioned such that its longitudinal axis lies at least parallel to the axis of rotation of the tomograph, in particular such that the axis of rotation lies in the tube, particularly preferably such that the center longitudinal axis of the at least one tube and the axis of rotation coincide.

In general, also the test body is positioned such that the isocenter of the tomograph lies in the interior of the at least one tube, preferably on its center longitudinal axis.

If the test body is positioned in such a way that the longitudinal axis does not lie exactly perpendicular to the plane of the sectional views, an elliptical shape is produced in the visual representation, on the basis of which the angular deviation between the longitudinal axis and the plane of the sectional view can be inferred.

A further important core idea of the invention is that the test body holds spheres of different diameters that is substantially formed by the stacked plates. The test body has at least one group of spheres with a first diameter and a group of spheres with a second diameter.

According to the invention, it can then be provided that these spheres of different diameter are used for the purpose of checking different transmission properties, for example on the one hand, to check the MTF with the larger/largest spheres and the geometric distortion with smaller than the largest spheres.

It is therefore possible to use a test body of the kind according to the invention for checking different properties of the tomograph without having to modify or change the test body.

The provision of spheres in addition to the at least one tube has the advantage that the sectional views of spheres always have a circular disk shape regardless of any angular deviation between the longitudinal axis of the at least one tube and the sectional planes, thus enabling the MTF to be determined based on these spheres, in particular based on some of the spheres (of the same diameter), in particular the spheres with the largest diameter.

A development can also provide that, based on the image reproduction of the cross sections of spheres with different diameter, in particular the spheres with a smaller diameter than the largest diameter, either the deviation of a sphere in the image reproduction from its known desired position is calculated or the deviations between one another of the spheres in the image reproduction from their known desired spacings are calculated.

At the same time, according to the invention, the materials of the components used in the test body, that is to say, for example, of the plates, of the at least one tube, and of the spheres, are selected depending on the measuring principle on which the tomograph to be tested is based.

With reference by way of example to a tomograph that works with X-radiation, it can accordingly be provided that the plates are chosen from a material that has absorption properties for X-radiation that are the same or at least similar to those of water. Such a material is basically disclosed in the prior art and is also referred to as "solid water." Therefore, in order to simulate water, it is possible, for example, to use certain plastics such as mixtures of different plastics such as polyethylene or polystyrene with titanium dioxide that are matched to one another in such a way that the same electron density as that exhibited by water is produced.

It can accordingly be provided that at least some of the plates, where applicable also all of the plates, of a test body according to the invention are chosen from such a material that has absorption properties like those of water, spheres of the different diameter and, where applicable, also the at least one tube that, for example, passes through the plates at right angles to the plane of the plates or at an angle deviating therefrom, being made of metal, for example of aluminum or also magnesium. Metals, in particular aluminum or magnesium, are known for having absorption properties for X-radiation that are similar to those of bones. Instead of at least one element that at least partially passes through the plates internally, such as at least one tube, also at least one external tube is around the plates, for example is provided in the form of external rods or as an external cage, in particular to which the plate or plates can be connected.

Here too it can then be provided that a test body with the, where applicable, plurality of tubes that do not lie on the same axis but preferably spacedly parallel to one another, is oriented in a tomograph for checking such that the tubes lie perpendicular to the sectional planes so that the sectional views of the tubes have a circular ring shape.

Compared with solid rods, the hollow design of the tubular rod in particular has the advantage of having fewer artifacts in the visual representations.

Here, it can be provided by way of a nonrestricting example that the outside diameter of the tube is chosen to be 14 mm and the wall thickness 4 mm. The parameters of outside diameter and wall thickness can preferably be chosen depending on the beam quality.

A test body suitable for an X-ray tomograph can accordingly be chosen as a result of the materials mentioned above.

If, on the other hand, tomographs that are based on the magnetic resonance principle are to be tested, also plates and spheres as well as the at least one tube are each chosen from non-metallic, but at least from non-magnetizable/non-magnetic materials, the spheres and the plates being chosen from different materials, in particular with different proton densities, for the purpose of achieving distinguishability in the visual reproduction of the tomograph.

According to the invention, spheres are used in the test body, as they are symmetrical and always exhibit a circular surface cross section that can easily be further evaluated, regardless of the position of the sectional plane in the visual reproduction of the layer images of an image stack.

As well as the above-mentioned spheres of at least two different diameters, spheres with a very small diameter that serve as so-called anchor points, are in the test body in order to correct the visual reproduction of the test body with regard to its position in the coordinate system on which the evaluation is based that is possible when the position of the spheres in the test body serving as anchor points as well as the position of the further spheres is known with sufficient accuracy. For example, the position of the spheres that are each integrated into the plates is specified with an accuracy of better than 0.1 mm.

In one embodiment, spheres with exactly three different diameters are used in the test body. Here, the smallest spheres serve as anchor points, in particular to mathematically correct the position of the test body for the evaluation, the spheres with medium diameter serve to check the geometric distortion between visual representation and the actual geometry, and the largest spheres serve to determine a measure of the modulation transmission function.

In an advantageous embodiment of the test body according to the invention, it can furthermore be provided that its external shape is based at least substantially on a human or animal body part. For example, a test body can be designed in such a way that the plates that are stacked and connected to the element substantially form a spherical shape in order to simulate a human head, for example. Here, it can be provided by way of example that the diameters of the individually stacked and in this case circular disk-shaped plates are reduced, where applicable in steps, in an outward direction starting from a central plate with the largest diameter.

In another embodiment, also plates with the same circular cross section, i.e. with the same diameter, or with a circular cross section (diameter) that changes in only one direction, are stacked and thus form a test body that is substantially cylindrical or that tapers in one direction, and that is substantially similar to an extremity of the human or an animal, such as an arm or a leg.

In yet another embodiment, also the individual plates are formed in such a way that the stack acquires the form of a female breast that in particular can be advantageous when tomographic devices for carrying out mammography are to be tested.

A tomograph can therefore be tested with regard to its transmission properties before carrying out an actual examination or also a medical application with a test body chosen depending upon the particular application.

Particularly in the case of rotationally symmetrical, for example cylindrical, test bodies, at least one tube can extend along or on its geometrical central axis, so that therefore the central longitudinal axis of the at least one tube and of the test body coincide.

In a preferred embodiment of the test body, it can furthermore be provided that the spheres are each in a recess in the surface of a plate that is covered by the flat surface of at least one adjacent plate or an opposing further recess in an adjacent plate. This provides a structurally easy way of integrating the spheres into the volume of the plates or of the material used for the plates.

In the simplest case, a particular sphere can be fully accommodated, i.e. with its whole volume, in a recess in a plate, for which purpose this plate has, for example, a cylindrical hole, where applicable a hole that passes completely through the plate. This hole can then, for example, be covered by the surface of one or even two (from both sides) adjacent contacting plates so that the position of a sphere positioned in the hole is fixed.

In another embodiment, it is also possible to make a hemispherically shaped recess in the surface of a plate that recess is covered by the contacting surface of an adjacent plate that likewise has a hemispherically shaped recess, wherein the two overlapping recesses complement one another to form an exactly spherical volume with the diameter of a sphere to be accommodated, so that, in such a case, a sphere accommodated between two plates with the center of the sphere exactly in the contact plane of the plates is accommodated without any inclusion of air.

In a simpler embodiment, also the recesses are not matched to the shape of a sphere, but each form mutually opposing cylindrical recesses/holes.

Particularly for the purpose of carrying out a later evaluation in conjunction with the method according to the invention, in a development, it can be provided that, depending on the size of a pixel or voxel (the surface unit or the volume unit in/from which the measured values are measured or the signal to be measured originates) of the recording sensors of a tomograph to be tested, some of the spheres, in particular those spheres with the largest diameter, are chosen in such a way that their diameter is 20 to 70 times this size.

It can therefore be provided that it must first be established which kind of tomograph is to be tested and, based on the size of the image or volume resolution of the recording sensors of this tomograph, for example of a computer tomograph based on X-radiation or of an MRT, the size of the sphere or the test body with appropriately matching sphere sizes to be used is then chosen.

Quite generally, for this purpose, it is possible for example to provide a set of a plurality of test bodies of the same or also of different shape that, as well as the possibility of simulating different body parts, are also matched with regard to the sphere sizes to the resolution (visual surface or volume resolution) of the tomographs to be tested, and, for the purpose of checking a tomograph, a user can therefore choose the suitable test body for checking from such a set of different test bodies. Here, in a possible embodiment, it can be provided, for example, that the sphere diameter of these spheres with the largest diameter within the test body lies in the range from 5-10 mm.

In a further embodiment, which in particular can be combined with the previous embodiment, some, in particular all, spheres with a smaller diameter than the largest diameter are chosen depending on the size of a pixel or voxel of the recording sensors (for example image sensor or volume element from which the signal originates) of a tomograph to be tested in such a way that its diameter is 10 to 20 times this size. Here, in particular, the three-dimensional imaging accuracy, i.e. geometric distortion of the tomograph, is tested with the spheres that are smaller than the maximum sphere diameter of all spheres present.

For this purpose, it is advantageous when these spheres have a smaller diameter than the largest diameter. Here, with these smaller spheres, a normal sphere diameter can lie in the range from 1 to 5 mm.

On the other hand, the spheres with the largest diameter can be used to obtain a measure of the modulation transmission function.

In a development that can be combined with all previously mentioned embodiments, the individual plates that contact one another are held together by an element that connects, for example passes through, the plates and that, for example, is designed with an annular cross section in the form of a tubular rod and passes through the individual plates exactly at right angles to the top or bottom surface of plate and forms a tube as mentioned in the introduction.

Another embodiment can provide that, although at least one tube is in the stack of plates, this has no connecting function. For example, the at least one tube, in particular tube, can be in a passage that is formed at least partially in the stack, i.e. at least runs through some of the plates that form the stack, where applicable passes through the stack completely. Each or at least some of the plates can have a throughgoing hole for this purpose. The throughgoing holes of the plates in the stack are in line to form the at least one passage.

When used as intended for checking a tomograph, a test body can be positioned in such a way, for example that the element connecting the plates, in particular the tubular rod, is oriented at right angles to the layer planes of the later layer images of the image stack.

This has the advantage mentioned in the introduction that the visual reproduction of the tubular rod in each of the layer images corresponds to an annular cross section. With this embodiment, as with the above-mentioned embodiment, in order to position the spheres in the volume of the body, these spheres can only be positioned in discrete areas within the volume of the test body.

These discrete areas are dependent on the positioning of the spheres in the test body and, for example, are determined by the contact plane of two adjacent plates or by the surface regions of a particular plate into which a particular sphere is completely or at least partially recessed.

For example, also a plate that accommodates spheres has throughgoing holes perpendicular to the plate surface, and therefore the volume for accommodating a sphere is determined by the overall thickness of the plate that is then contacted by two adjacent plates to close off this volume and to accommodate the spheres. In such a case, spheres can only be positioned discretely with their respective centers in the middle of the respective accommodating plates.

In order to not only enable spheres to be in discrete positions inside the test body, in a development, the contact planes in which the mutually contacting surfaces of adjacent plates lie, lie for example deviating from a perpendicular arrangement is relative to the tube. For example, an angular range of plus/minus 30° about the perpendicular arrangement can be chosen.

If a test body of this embodiment is positioned in a tomograph for the testing thereof in such a way that, in the visual reproduction, the tube runs perpendicular to the layer planes of the image stack, then the contact planes of the individual plates no longer lie parallel to the individual layers of the image stack but at a different angle (from 0 to 180°) thereto so that the spheres that are in or between adjacent plates can assume different heights relative to the individual layer images.

For example, if a test body with at least one tube is not necessarily in a tomograph to be tested in such a way that, in the later layer image sequence, the tube runs perpendicular to the layer plane, it can generally be provided that, when the test body is as intended in a tomograph to be tested, the contact planes of the mutually contacting surfaces of adjacent plates do not lie or are not laid parallel to the planes of the sectional images of a sectional image stack calculated by the tomograph or an external evaluation unit in order to achieve this above-described advantage.

Accordingly, one of the two above-mentioned embodiments makes it possible for the visual reproductions of the spheres in a particular layer image to have different cross sectional sizes, even when the spheres present in the visual reproduction actually all have the same diameter, as, with the embodiment mentioned above, these spheres are cut at different heights in the respective layer images.

A method of checking the transmission properties of a tomograph preferably uses a test body according to the invention, in particular of the kind described above.

Here, in one embodiment, it can be provided that, for calculating a measure of the modulation transmission function (MTF), in at least one of the layer images, preferably in all layer images, at least one image reproduction of the cross section of a sphere or of the cross section of the at least one tube is selected by image recognition software or also by manual selection by an operator in order to then evaluate this so selected or chosen cross sectional image of the sphere or of the tube with regard to the measure of the modulation transmission function.

Basically regardless of how the visual reproduction of a sphere or of the tube is identified within a sectional image, all intensity measurements of pixels or voxels that represent a visual reproduction of at least one cross section of a sphere, in particular of such with the largest diameter, or of at least one tube, and that, within a specified tolerance interval, are at the same radial distance from the center of the visual reproduction, are averaged in order to calculate a measure of the modulation transmission function. For this purpose, it can be provided, for example, that this center is determined automatically by image evaluation.

Here, averaging means that the intensity measurements of these pixels/voxels each having the same radial distance are summed, and the result of this sum is divided by the number of the summed pixels/voxels. This method variation enables a kind of over-sampling to be carried out, as the distance between radii becomes less than the individual detector element or volume element from which the signal originates (sensor pixel or voxel).

In an advantageous development, it is then possible to fit or form a function, for example a polynomial, for the functional dependency of the averaged intensity measurements on the radius. Within the meaning of the invention, this formed/fitted function then constitutes a measure, with whose help the modulation transmission function (MTF) can be determined. The MTF can be used to check the quality of the tomograph.

As mentioned in the introduction, those spheres that have a smaller diameter than the spheres with the largest diameter within the test body are preferably used to check the tomograph or its evaluation software (rear-projection algorithm) with regard to geometric distortions, i.e. with regard to the 3D imaging accuracy.

The positions of the spheres within the test body is therefore known, for example relative to the center of the test body that, in an illustrated embodiment, can lie axially in the center of the at least one tube.

With a knowledge of these known positions of the spheres, it is then possible within the visual reproductions, i.e. the representation of the spheres in the individual layer images or a 3D representation compiled from the layer images, to determine the deviation either of the spheres from the desired position or the relative deviation of spheres from one another, and to visualize the magnitude of the deviation in the layer image or in the formed 3D representation for each of the spheres examined in accordance with this criterion.

In one embodiment, in order to carry out such a visualization, for example the sphere reproductions are marked in color in the layer images or in the 3D representation, the colors depending on the magnitude of the deviation. The deviations can also be reproduced as a numerical value, for example as a percentage. As a result, the deviations from the desired positions or the geometric distortions are visually easy for an observer to distinguish. Such results can be used, for example, to optimize the evaluation algorithms or rear-projection algorithms, or also to enable the images of different tomographs to be matched.

A development that can be combined with any of the above-mentioned embodiments can provide that at least one sensor is in at least one of the tubes, where applicable in the single tube. Such a sensor can be used, for example, to measure the radiation dose that occurs during a test. As a systematic mismeasurement of the actual dose occurs due to the at least partial screening of radiation, for example X-radiation, by the material of the tube, the measurements are corrected after recording, for example based on the known actual screening.

On the other hand, in order to avoid screening effects, a preferred embodiment can provide that at least one passage that passes through at least some of the plates, is in the stack of plates. As well as the possibility of inserting tubes made of different materials into the passage, depending on the application, it is also possible here to arrange at least two tubes, in particular tubes of circularly annular cross section that are spaced apart axially, in the at least one passage.

In this way, a space is formed between two such tubes in the interior of the plate stack, preferably in the center thereof that is not surrounded by the material of the tube, in particular therefore free from screening metal. With this embodiment, at least one sensor, for example for detecting the radiation dose during the test, is in this space, for example by sliding at least one such sensor into the space through one of the tubes or also, where applicable, a plurality thereof.

Such a sensor can be formed, for example, by so-called solid-state detectors, diodes, thermoluminescent crystals or similar.

For example, in this way, series of measurements can be normalized or compared with one another based on the dose measurements that are recorded in parallel. It is also possible to check a tomograph depending on the dose and therefore to determine test results that are dependent on the dose, in particular MTF or geometric distortions.

For example, a minimum radiation dose for a possibly subsequent patient examination can be determined in order to obtain qualitatively perfect images, as a result of which patients are treated with care. Accordingly, a dose can be set as high as necessary and as low as possible based on the dose-dependent test measurements.

Furthermore, the design of a test body with plate stack and at least one passage with at least one tube therein has the advantage that a retaining device for holding a test body in a tomograph to be tested can reach at least partially into the interior of at least one tube, where applicable even reach completely through the test body. For example, a test body with at least one tube reaching through all plates can be threaded onto a retaining rod or retaining strip. Also, a laser beam can be guided through the interior of the at least one tube in order to adjust a test body, for example on an isocenter of a tomograph.

According to a further development that can be combined with any of the above-mentioned embodiments in addition to at least one tube or at least two tubes lying behind one another with axial spacing, a plurality of rods, in particular made from solid material that are around at least one of the tubes, are provided in the plate stack. Here, each of the rods can be parallel or preferably at an angle other than 0°, for example at an angle of up to 10°. For example, each of the additional rods can converge with that tube about which it is arranged.

At the same time, a preferred embodiment can provide that the additional rods only extend into some of the plates. For example, the additional rods can extend into the stack starting from a last/first plate of the plate stack, for example only over an area of not more than 50% of the total stack length (measured in a direction perpendicular to the contact planes of the plates), preferably not more than 30% of the total stack length. With regard to their diameter, the additional rods are preferably smaller than the at least one tube, in particular the tube they surround.

A test body with one of the above-mentioned embodiments of the additional rods can be used to record at least one first image or a first series of images therein, and at least one second image or a second series of images, the first and second images or series of images being offset axially of the tube that is surrounded by the rods. It is therefore possible to combine the first and second images or series of images and therefore to check whether a lateral and/or axial offset is present or not present in the case of the additional rods in the combined image or the combined series of images. This enables the so-called "stitching" or combining process of images to be tested. Such a process is necessary, for example, when separate images of the top and bottom jaw, which are to be subsequently combined to form an overall view, are created with a tomograph. For this purpose, it is important to know that the "stitching" process and the creation of the separate images/series of images are carried out correctly.

The particular tomograph under examination can be identifiably tested with regard to its transmission properties based on a plurality of criteria simultaneously by a single series of recordings using a test body and a method of the kind according to the invention. One and the same image stack, comprising a plurality of layer images, can be simultaneously or successively examined with regard to these criteria using evaluation software in order to obtain a measure of the investigated criterion.

BRIEF DESCRIPTION OF THE DRAWING

Embodiments of the invention are explained in more detail with reference to the following figures:

FIG. 4b is a section taken along line IVb-IVb of FIG. 4a; and

SPECIFIC DESCRIPTION OF THE INVENTION

In a side view and in plan, FIGS. 1a-1d show a test body 1 according to the invention that is made up of a plurality of plates 2 that are stacked on top of one another and that here are connected by a cylindrically tubular rod 3 that passes through the plates 2 centrally. In this embodiment, the tube 3 is formed from aluminum and has threads at its ends in order to press the plates 2 against one another by nuts on these threaded ends.

As described in the general part, the invention is not restricted to such a design. Also at least one tube that does not perform the function of connecting the plates 2, can provided in or outside the stack.

According to the embodiments discussed above, a plurality of spheres 4 that according to the invention have at least two different diameters can be provided on the faces of the individual plates 2 or between two adjacent plates 2. FIG. 1b shows this while omitting the plates 2. There are therefore at least spheres of a first group with a large diameter and spheres of a second group with a small diameter, the spheres from the group with the larger or largest diameter of all spheres being provided to determine a measure of the MTF, and the spheres with a smaller diameter than the largest diameter being provided to determine the geometric imaging accuracy or the distortion of the tomograph or of the evaluation algorithms that it is using. According to the invention, the MTF can also be determined based on the at least one tube 3, as needed exclusively or in combination with spheres.

Regardless of the shape of a test body 1, a larger number of the smaller spheres are provided for determining the distortion than are provided of the larger/largest spheres.

In the case of a ball-shaped test body, as shown here, at least one of the larger/largest spheres is provided per octant of the spherical test body.

Figure 1A:
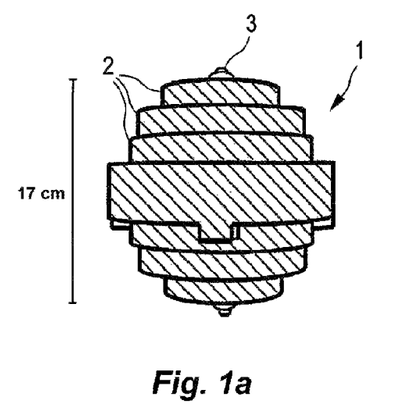
FIG. 1a is a side view of the test body according to the invention.
Figure 1B:
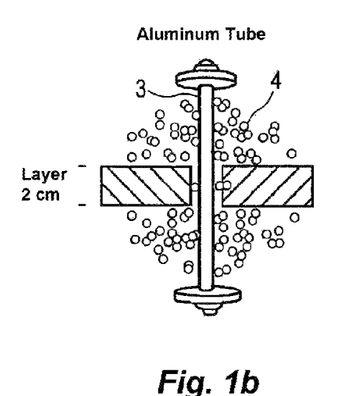
FIG. 1b is an axial section through the test body with only the center plate shown.
Figure 1C:
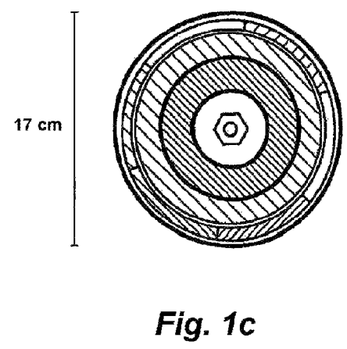
FIG. 1c is a top view of the test body.
Figure 1D:
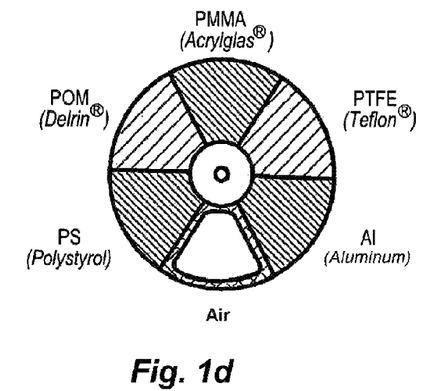
FIG. 1d is a top view showing a possible plate construction according to the invention.

Here, FIG. 1a shows an external view of such a test body 1 that is substantially spherically ball-shaped and therefore represents a head of a human being that, for example, is to be measured with the tomograph in a subsequent examination or treatment.

Here, this spherical shape is approximately formed in that, starting from a central plate with circular cross section and the largest diameter, further plates with diameters that become successively smaller in steps are stacked above and below this plate so that the diameter of the test body upward and downward is reduced in steps. This results in an approximately spherical shape with a diameter specified here by way of example of 17 cm.

Of course, any other dimensions are possible here, as well as other designs of the test body in order to simulate other body parts.

Figure 2:
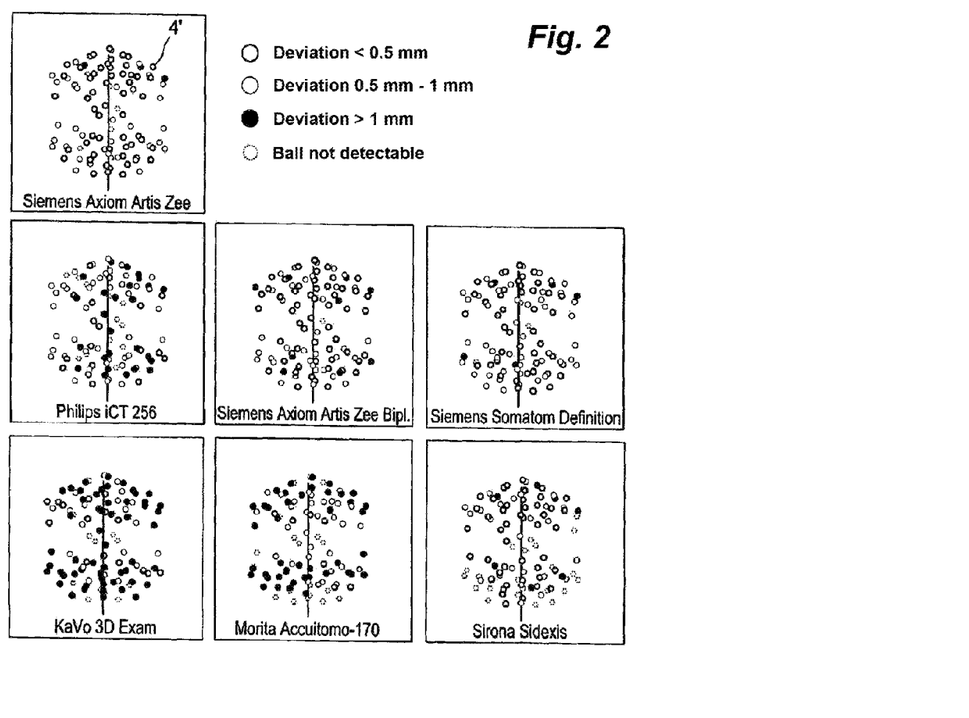
FIG. 2 shows 3D views taken according to the invention by various tomographs.

FIG. 2 is 3D views that are formed from the individual layer images of an image stack, the position of the individual spheres in the particular representation being represented by their visual reproductions.

Here, FIG. 2 shows the recordings that have been made or calculated with the same test body 1 for different tomographs or manufacturers thereof. Here, the individual spheres or their visual reproduction 4' in the image stack have been investigated to establish how great the deviation of the visual representation of a sphere 4 is compared with the actual desired position in the test body, where the magnitude of the deviation established is marked in color.

It can be seen here that different tomographs produce different deviations and therefore different imaging errors in the visual reproduction of the test body even though they are measuring the same test body.

Accordingly, with a knowledge of these deviations, it is also possible to match visual reproductions of different tomographs to one another using one and the same test body, for example in order to examine or treat the actual body part in a later application, for example in diagnostic examinations or therapy, using different types of tomographic method.

For example, it is possible to match, i.e. to superimpose, tomographic images of a magnetic resonance tomograph with the X-ray images of a computer tomograph when, namely, on the one hand, such a test body that opens up the possibility of reproducing the spheres in the individual X-ray layer images is used to determine the geometric distortion of the computer tomograph and, on the other, to check an MRT with one test body, plastic spheres or at least non-magnetic/non-magnetizable spheres being used in this test body instead of, for example, metallic spheres. Here, the two different test bodies are formed only from different materials with regard to the plates and spheres, but have the same size and shape, in particular with the same manufacturing tolerances.

Figure 3:
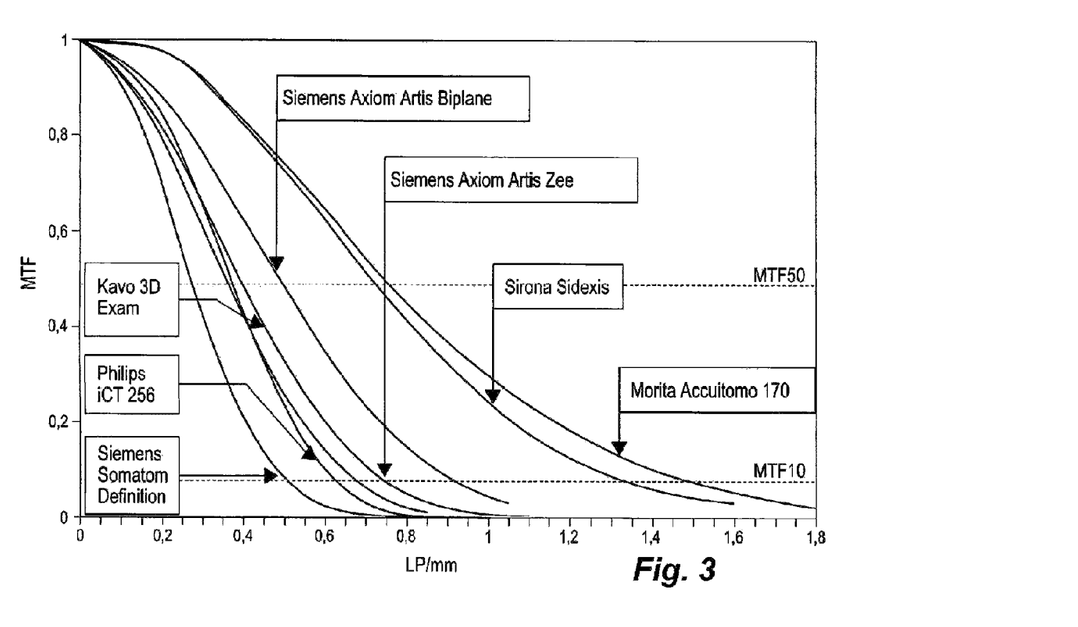
FIG. 3 is a graph illustrating the MTF with various tomographs.

Furthermore, FIG. 3 shows that, based on the larger or largest spheres and/or the at least one tube 3, it is possible to check the modulation transmission function by the same test body with different tomographs. Here, the results of FIGS. 2 and 3 can be determined from the same series of measurements.

Here, FIG. 3 represents the modulation transmission function for the different tomographs tested by way of the graph shown that plots the MTF against the radius. Preferably, according to the invention, the MTF is determined as mentioned in the general part of the description described in the introduction, in particular with the over-sampling principle described therein.

Here too, it can be seen that, when using the same test body as shown in FIGS. 1a-1d, this results in different modulation transmission functions of the different tomographs. Accordingly, these different tomographs with the different modulation transmission functions can be compared with one another and therefore chosen specifically for the application.

Figure 4A:
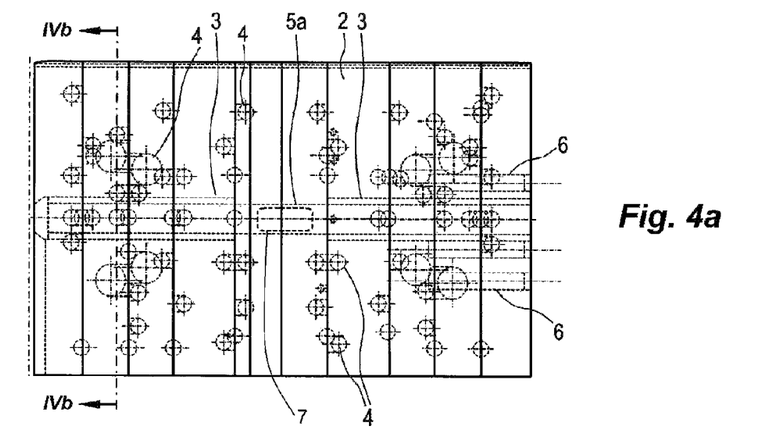
FIG. 4a is a side view of another test body in accordance with the invention.
Figure 4B:
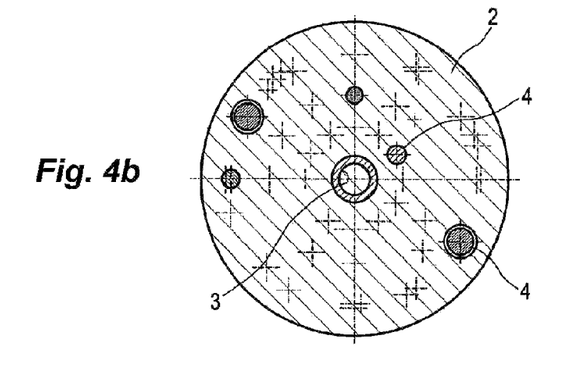

FIGS. 4a and 4b show a cylindrical test body that is made up of a plurality of axially stacked plates 2. The left-hand sectional view shows, in one plate, the spheres 4 of different diameter therein and also—here centrally—at least one tube 3, for example made of metal such as aluminum or magnesium, in the circular plate 2. The advantage here is that the tube 3 extends through a plurality of plates 2 and thus provides the same circular image in a plurality of layer images, thus enabling the MTF to be tested in this plurality of layer images based on the same criterion in all cases.

Figure 5:
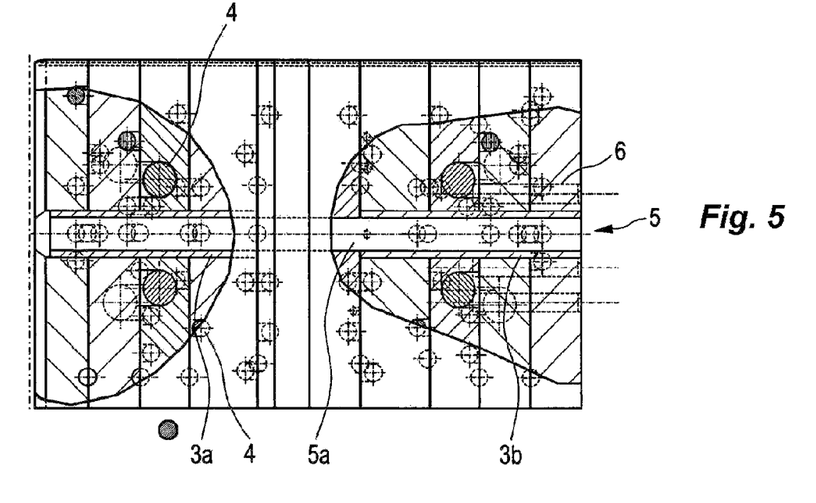
FIG. 5 is a partly sectional view of the body of FIGS. 4a and 4b.

FIG. 4b also shows a possible development with a plurality of additional rods 6 that are shown dashed and all converge on the right-hand tube 3. The additional rods are only around the right-hand tube and here preferably only over a part of its length, in particular starting from a cover plate of the stack. FIG. 5 also shows this as a possible dashed development.

FIG. 5 shows an embodiment in which a test body, here by way of example cylindrical, has an internal passage 5 into which two tubes 3a and 3b that are axially aligned but axially spaced are inserted. As a result of the spacing, an inner free passage region 5a is produced between the tubes 3a and 3b that is not surrounded by raw material, in particular therefore not by metal, and into which, for example, a sensor 7, or another device can be inserted in order to record additional measurements of the layer images such as, for example, the radiation dose that was used. FIG. 4b also shows this free passage region 5a.

A significant advantage according to the invention lies in that both the modulation transmission function and also a measure of the geometric distortions can be obtained from the same data record that is produced with one and the same test body during the tomographic recording, where applicable with measurement of a radiation dose or other measured values.

Not shown is the fact that the noise-power spectrum and the signal-noise ratio can also be tested with a test body of the kind according to the invention. Algorithms that are basically known from the prior art can be called upon here, however using the test body according to the invention.

As a general principle, in a development, also a test body of the kind described in the general part or in the execution part is used in a further body, in particular in a test body, likewise of the kind described above, but with an internal free volume. This enables a modular system to be created.

The invention claimed is:

1. A test body for checking the transmission properties of radiological tomographs, the test body comprising:
    a plurality of plates connected to form a stack in which adjacent plates contact each other, one of the plates being formed with a plurality of recesses,
    spheres made of at least one material different from the plates, of at least two different diameters, each in a respective one of the recesses, and each engaging an adjacent one of the plates, the spheres being in or between the one of the plates and the adjacent plate, and
    a tube is on/in the stack.

2. The test body as claimed in claim 1, wherein the tube passes through the plates forming the stacks and connects the plates forming the stack to one another.

3. The test body as claimed in claim 1, further comprising:
    a sensor in the tube for measuring a radiation dose that occurs during a test.

4. The test body as claimed in claim 1, wherein the stack forms a passage holding the tube removably.

5. The test body as claimed in claim 4, wherein two of the tubes that are axially aligned and axially spaced are in the passage.

6. The test body as claimed in claim 5, further comprising:
    a sensor for measuring a radiation dose that occurs during a test in the passage in a space between the two tubes.

7. The test body as claimed in claim 1, wherein the stack has an external shape corresponding at least substantially to a human or animal body part.

8. The test body as claimed in claim 1, wherein the sphere diameter lies between 5 and 10 mm.

9. The test body as claimed in claim 1, wherein the sphere diameter is between 1 and 5 mm.

10. The test body as claimed in claim 1, wherein the adjacent plate is also formed with recesses in which the spheres are also partly received.

11. The test body as claimed in claim 1, wherein the recesses of the one plate are throughgoing cylindrical holes.

* * * * *